(12) United States Patent
Albrecht et al.

(10) Patent No.: US 7,279,449 B2
(45) Date of Patent: Oct. 9, 2007

(54) HAIR SHAMPOO CONTAINING PREGELATINIZED, CROSS-LINKED STARCH DERIVATIVES

(75) Inventors: Harald Albrecht, Hamburg (DE); Birgit Heitmann, Hamburg (DE); Stephan Ruppert, Hamburg (DE)

(73) Assignee: Beiersdorf AG, Hamburg (DE)

( * ) Notice: Subject to any disclaimer, the term of this patent is extended or adjusted under 35 U.S.C. 154(b) by 121 days.

(21) Appl. No.: 10/511,123

(22) PCT Filed: Apr. 9, 2003

(86) PCT No.: PCT/EP03/03680

§ 371 (c)(1),
(2), (4) Date: Jun. 29, 2005

(87) PCT Pub. No.: WO03/084488

PCT Pub. Date: Oct. 16, 2003

(65) Prior Publication Data

US 2006/0178288 A1    Aug. 10, 2006

(30) Foreign Application Priority Data

Apr. 11, 2002    (DE) ............... 102 16 497

(51) Int. Cl.
C11D 3/22 (2006.01)
C11D 1/00 (2006.01)
C11D 3/37 (2006.01)
A61K 8/40 (2006.01)
A61K 8/60 (2006.01)

(52) U.S. Cl. ............ 510/121; 510/127; 510/151; 510/413; 510/414; 510/474; 510/492; 510/504; 424/401; 424/70.13; 424/70.21; 424/70.22; 424/70.31

(58) Field of Classification Search ........ 510/121, 510/127, 151, 413, 414, 474, 492, 504; 424/401, 424/70.13, 70.21, 70.22, 70.31
See application file for complete search history.

(56) References Cited

U.S. PATENT DOCUMENTS

| 4,508,705 A | 4/1985 | Chaudhuri et al. |
|---|---|---|
| 5,520,200 A | 5/1996 | Sturla |
| 5,653,988 A | 8/1997 | Gerber et al. |
| 5,869,070 A | 2/1999 | Dixon et al. |
| 5,871,756 A | 2/1999 | Jeffcoat et al. |
| 5,900,241 A | 5/1999 | Roulier et al. |
| 5,925,380 A | 7/1999 | Roulier et al. |
| 6,033,680 A | 3/2000 | Dixon et al. |
| 6,248,338 B1 * | 6/2001 | Muller et al. ............ 424/401 |
| 6,294,180 B1 | 9/2001 | Demars et al. |
| 6,322,818 B1 | 11/2001 | Rebier |
| 6,413,505 B1 | 7/2002 | Vitale et al. |
| 2001/0007655 A1 | 7/2001 | Paul et al. |
| 2001/0018046 A1 | 8/2001 | Vitale et al. |
| 2003/0035783 A1 | 2/2003 | Birkel et al. |

FOREIGN PATENT DOCUMENTS

| DE | 199 21 707 | | 11/2000 |
|---|---|---|---|
| DE | 201 09 450 | | 1/2002 |
| EP | 0 968 703 A1 | | 1/2000 |
| GB | 1 285 547 A | | 8/1970 |
| GB | 2 366 727 | | 3/2002 |
| WO | WO98/01109 | * | 1/1998 |
| WO | WO - 99/33437 A1 | | 7/1999 |
| WO | WO - 99/64508 | | 12/1999 |
| WO | WO 01/19404 A1 | | 3/2001 |

OTHER PUBLICATIONS

International Search Report from International Application No. PCT/EP03/03677, dated Aug. 11, 2003.
International Search Report from International Application No. PCT/EP03/03678, dated Aug. 11, 2003.
International Search Report from International Application No. PCT/EP03/03679, dated Aug. 1, 2003.
International Search Report from International Application No. PCT/EP03/03680, dated Aug. 5, 2003.
International Search Report from International Application No. PCT/EP03/03610, dated Jul. 14, 2003.
International Search Report from International Application No. PCT/EP03/03611, dated Sep. 5, 2003.

* cited by examiner

Primary Examiner—Brian Mruk
(74) Attorney, Agent, or Firm—Greenblum & Bernstein, P.L.C.

(57) ABSTRACT

The present invention is a polymer-containing cosmetic hair shampoo comprising one or more pregelatinized, crosslinked starch derivatives. Preferably, the hair care agent further comprises one or more polymers. In one embodiment, the polymer includes cationic polymers. In another embodiment, the polymer includes nonionic, amphoteric, or anionic polymers.

17 Claims, No Drawings

HAIR SHAMPOO CONTAINING PREGELATINIZED, CROSS-LINKED STARCH DERIVATIVES

FIELD OF THE INVENTION

The present invention relates to cosmetic hair shampoos with improved haircare performance, in particular those a content of starch derivatives which achieve especially improved combability, hair volume and/or body, shine and improved feel upon use.

BACKGROUND OF THE INVENTION

The entire human body, with the exception of the lips, the palms of the hands and the soles of the feet, is covered in hair, for the large part, however, with barely visible down. Because of the many nerve endings at the hair root, hair reacts sensitively to external influences such as wind or touch and is therefore a component of the sense of touch that should not be underestimated. The most important function of human head hair must, however, nowadays consist in helping to create the appearance of the person in a characteristic manner. Similarly to the skin, it fulfills a social function since, via its outward appearance, it contributes considerably to interpersonal relations and to the self-esteem of the individual.

The hair consists of the hair shaft which protrudes freely from the skin—the keratinized (dead) section which represents the actual visible hair—and the hair root which sticks in the skin—the living section, in which the visible hair is continually renewed. The hair shaft in turn is made up of three layers: a central section—the so-called hair marrow (medulla), which, however, in humans has retrogressed and is often missing altogether—also the marrow (cortex) and the external, horny layer up to ten layers thick (cuticle), which surrounds the entire hair.

Provided there are no pathological changes, it is virtually impossible to improve upon human hair in its freshly grown state. The section of a hair in the vicinity of the scalp accordingly has a virtually closed horny layer. In particular, the horny layer, being the external sheath of the hair, but also the inner region below the cuticle, are exposed to particular stress by environmental influences.

Significant effects on the loss of quality of a hair during its ageing are the effect of sunlight, mechanical stresses as a result of intensive combing or brushing, but also hair treatments, such as hair colorings and in particular bleachings, and hair shapings, for example permanent waving processes. Accordingly, oxidative stresses in particular often lead to hair damage.

Both UV-A and also UV-B radiation have a harmful effect on the hair, which is evident, for example, from the fact that certain amino acids, such as cystine and methionine are degraded or sulfur-sulfur bonds of keratin are cleaved, which in the worst case scenario can result in destruction of the hair. In addition, hair and scalp represent parts of the body which, due to their position, are subjected to a considerable amount of UV radiation when outdoors.

One aim of hair care is to maintain the natural condition of freshly grown hair over the longest period possible and, if it is lost, to restore it. Silky sheen, low porosity and a pleasant smooth feel are features of natural healthy hair.

Since the end of the previous century products for hair care have been developed specifically. This led to a large number of preparations both for general hair care and also for alleviating the anomalies of hair and of the scalp. In general, use is nowadays made of hair care cosmetics which are, after they have worked, either intended to be washed out of the hair again, or which should remain on the hair. The latter can be formulated such that they not only serve to care for the individual hair, but also improve the appearance of a hair style overall. Hair cared for in such a way is characterized by a pleasant feel, natural shine, increased body, suppleness and thus good stylability and strength and thus good hairstyle sit.

Modern cleansing products for cleansing the hair generally consist of water, surfactants, thickeners, auxiliaries and care components.

The care components in particular have recently achieved great significance since the consumer, particularly one with stressed or damaged hair, expects a very high care performance. Care here is synonymous with the biophysical parameters combability, volume, body, shine, feel.

In order to obtain a correspondingly high care performance, oils, preferably silicone oils, can be incorporated into the shampoo formulations. Formally, these formulations are emulsions which accordingly also have a white, creamy appearance. However, the preparation of these emulsions in stable form requires complex formulation technology.

A further disadvantage consists in the fact that although the silicone oil used attaches to the hair, which produces the abovementioned care effect, it also leads to a deposit-forming effect of the oil on the hair if the hair is washed often: a layer of silicone oil which increases with each use forms on the hair. The regular use of such an emulsion leads to a decrease in the hair volume and the body due to the increasing weighing down of the hair with oil. The use of starch derivatives could not overcome the described disadvantages of the prior art in the past either.

It has been found, in a manner which is surprising and unforeseeable by the person skilled in the art, that cosmetic hair cleansers comprising one or more pregelatinized, crosslinked starch derivatives, cationic polymers and nonionic, amphoteric and/or anionic surfactants overcome the disadvantages of the prior art. By using the preparations according to the invention, excellent care performances have been obtained which are at least equivalent to the care performance of a silicone shampoo.

These do not have the depot-forming effects of emulsion shampoos which weigh down the hair either, but also lead, upon frequent and regular use, to an excellent care performance with regard to body and volume.

In this way, it is also possible to prepare transparent formulations.

The invention also covers the use of one or more pregelatinized, crosslinked starch derivatives for improving the combability, the volume, the body, the shine, the feel of hair treated with hair cleansers comprising cationic polymers and nonionic, amphoteric and/or anionic surfactants.

As pregelatinized, crosslinked starch derivatives, particular preference is given to using hydroxypropylated phosphate esters, very particularly preferably hydroxypropyl distarch phosphates.

Very particular preference is given to hair cleansers or uses according to the invention characterized in that the content of pregelatinized, crosslinked starch derivatives is 0.1-20% by weight, preferably 0.3-15% by weight, particularly preferably 0.5-10% by weight. Preference is given to hair cleansers or uses according to the invention characterized in that the content of cationic polymers is 0.1-15% by weight, preferably 0.2-8% by weight, particularly preferably 0.3-5% by weight. The cationic polymers particularly preferably used are polymeric quaternized ammonium salts of hydroxyethylcellulose which has been modified with a trimethylammonium-substituted epoxide, depolymerized and subsequently quaternized guar gum derivatives and/or quaternized guar derivatives.

Preference is given to hair cleansers or uses according to the invention characterized in that the nonionic, amphoteric and/or anionic surfactants used are ethoxylated and sulfated fatty alcohols with 12 to 14 and/or alkylamidopropylbetaine.

Preference is also given to hair cleansers or uses according to the invention characterized in that further surfactants and/or cosmetic or dermatological auxiliaries, additives and/or active ingredients are additionally present.

Although U.S. Pat. No. 6,248,338 describes cosmetic preparations with pregelatinized, crosslinked starch derivatives, this specification was unable to point the way to the present invention.

According to the invention, it is advantageous if the pregelatinized, crosslinked starch derivatives used are hydroxypropylated phosphate esters. Of particular advantage are those starch derivatives as described in U.S. Pat. No. 6,248,338, particularly advantageously hydroxypropyl distarch phosphate. Very particular preference here is given to the use of a hydroxypropyl distarch phosphate, as is sold in the form of the product Structure® XL by National Starch.

The use of polymeric quaternized ammonium salts of hydroxyethylcellulose, which has been modified with a trimethylammonium-substituted epoxide, with the INCI name Polyquaternium-10, as are supplied under the name Ucare Polymer JR 400 by Amerchol, or the use of depolymerized guar gum derivatives which have been quaternized, for example those with the INCI name Guar Hydroxypropyl Trimonium Chloride, as are sold under the name Jaguar Excel by Rhodia is advantageous. Here, the combination of starch derivatives with the specified polymers improves the suppleness-improving care properties in a synergistic manner without weighing down the hair. At the same time, the hair is given a pleasant feel sensation and can be styled easily.

The hair cosmetic cleansers and preparations which comprise the active ingredients according to the invention are topical preparations. These can have the customary composition and be used for the treatment and the care of the scalp and/or the hair or as photoprotective preparation. For use, the preparations according to the invention are applied to the scalp and the hair in an adequate amount in the manner customary for cosmetics and hair cleansers.

For the purposes of the present invention, preparations may advantageously be in the form of emulsions or solutions.

The compositions according to the invention can, for example, be in the form of preparations which can be dosed from squeezable bottles or via a pump or spray device, but also in particular in the form of a composition which can be applied from normal bottles and containers.

Preparations according to the invention, which represent hair cosmetic cleansing preparations for the hair and/or the scalp, can be in liquid or solid form. They preferably comprise at least one anionic, nonionic or amphoteric surface-active substance or mixtures thereof, optionally an electrolyte and auxiliaries as are customarily used for this purpose. The surface-active substance can be present in a concentration between 1 and 94% by weight in the cleansing preparations, based on the total weight of the preparations, but in particular is between 1 and 50% by weight.

In particular, aqueous cosmetic cleansers according to the invention or low-water or anhydrous cleanser concentrates intended for aqueous cleaning can comprise anionic, nonionic and/or amphoteric surfactants, for example conventional soaps, e.g. fatty acid salts of sodium, alkyl sulfates, alkyl ether sulfates, alkane- and alkylbenzenesulfonates, sulfoacetates, sulfobetaines, sarcosinates, amidosulfobetaines, sulfosuccinates, sulfo-succinic half-esters, alkyl ether carboxylates, protein fatty acid condensates, alkylbetaines and amidobetaines, fatty acid alkanolamides, polyglycol ether derivatives.

Anionic surfactants are preferably used in concentrations between 5% by weight and 20% by weight. Of suitability are, for example, sodium laureth sulfate, as is supplied under the name Texapon N 70 by Henkel, or disodium laureth sulfosuccinate, as is supplied under the name Rewopol SBFA 30 by Witco. Nonionic surfactants are preferably used in concentrations of from 1% by weight to 10% by weight. Examples are decyl glucoside, as is supplied under the name Oramix NS 10 by Seppic, or polysorbate 80, as is supplied under the name Tween 80 by ICI. Amphoteric surfactants are preferably used in concentrations of from 1% by weight to 10% by weight. Examples are cocamidopropylbetaine, as is supplied in the form of Tego Betain by Goldschmidt, or sodium cocoamphoacetate, as is supplied under the name Miranol Ultra by Rhone Poulenc.

The percentages refer to the total weight of the preparations.

In addition, conditioning auxiliaries may be present in the hair cosmetic cleansers, e.g. in amounts of from 0.001 to 10% by weight, based on the total weight of the preparations. Preferred conditioning auxiliaries include polymeric quaternary compounds (quats). Polymeric quats are used widely in shampoos, e.g. in a concentration of from 0.01 to 2% by weight. These include polyquaternium-10, as is supplied under the name Polymer JR 400 by Amerchol, or hydroxypropyl guar hydroxypropyltrimonium chloride, as is supplied with the name Jaguar C 162 by Rhone-Poulenc.

The preparations according to the invention can comprise cosmetic auxiliaries as are customarily used in such preparations, e.g. preservatives, perfumes, substances for preventing foaming, foam stabilizers, dyes, pigments which have a coloring effect, thickeners, surface-active substances, emulsifiers, softening, moisturizing and/or humectant substances, refatting agents, fats, oils, waxes, alcohols, polyols and toxicologically compatible ethers and esters thereof, branched and/or unbranched hydrocarbons, further antioxidants, stabilizers, pH regulators, bodying agents, bactericides, deodorants, antimicrobial substances, antistats, UV absorbers, complexing and sequestering agents, pearlizing agents, polymers, electrolytes, organic solvents, silicone derivatives, plant extracts, vitamins and/or other active ingredients or other customary constituents of a cosmetic or dermatological formulation. Solubility promoters, e.g. for incorporating hydrophobic components, such as, for example, perfume preparations, may also be present.

The total amount of the auxiliaries is, for example, 0.001 to 15% by weight, preferably 0.01 to 10% by weight, in each case based on the total weight of the preparation.

The water content of the preparations is, for example, 50 to 95% by weight, preferably 55 to 90% by weight, in each case based on the total weight of the preparation.

According to the invention, further antioxidants which may be used are all antioxidants customary or suitable for cosmetic and/or dermatological applications.

The total amount of the antioxidants is, for example, 0.000.001 to 2% by weight, preferably 0.0001 to 1% by weight, in each case based on the total weight of the preparation.

Further antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to pmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of the specified active ingredients which are suitable according to the invention.

Preparations according to the invention may advantageously also comprise substances which absorb UV radiation in the UV-B region, where the total amount of the filter substances is, for example, 0.001% by weight to 30% by weight, preferably 0.05 to 10% by weight, in particular 0.1 to 1.0% by weight, based on the total weight of the preparations, in order to provide cosmetic preparations which protect the hair and/or the skin from the entire range of ultraviolet radiation. They can also serve as sunscreens for the hair or the skin, in particular the scalp.

If the emulsions according to the invention comprise UV-B filter substances, these may advantageously be water-soluble. Advantageous water-soluble UV-B filters are, for example:

salts of 2-phenylbenzimidazole-5-sulfonic acid, such as its sodium, potassium or its triethanolammonium salt, and the 2-phenylbenzimidazole-5-sulfonic acid itself;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)benzenesulfonic acid, 2-methyl-5-(2-oxo-3-bornylidene-methyl) sulfonic acid and its salts.

It may also be advantageous to admix preparations according to the invention with UV-A filters which are hitherto customarily present in cosmetic preparations. It is possible to use the amounts used for the UV-B combination.

The preparations according to the invention can be prepared in the customary manner by mixing the individual constituents. The active ingredients of the combinations according to the invention or else the premixed constituents of the combinations according to the invention may be added in the mixing operation.

The pH of the preparations can be adjusted in a known manner by adding acids or bases, preferably by adding buffer mixtures, e.g. based on citric acid/citrate or phosphoric acid phosphate buffer mixtures. Preferably, the pH is below 10, e.g. in the range from 4-8, in particular in the range from 5-7.

Unless stated otherwise, all amounts, fractions and percentages are based on the weight and the total amount or on the total weight of the preparations or of the particular mixture.

The examples below illustrate the invention.

The amounts given in the examples are percentages by weight, based on the total weight of the particular preparation.

Examples of Hair Shampoo Formulations

|  | 1 | 2 | 3 | 4 | 5 | 6 |
|---|---|---|---|---|---|---|
| Sodium lauryl ether sulfate | 9 | 9 | 9 | 9 | 9 | 11 |
| Sodium myristyl ether sulfate | — | — | — | — | — | 2 |
| Cocamidopropylbetaine | 4 | 4 | 4 | 4 | 4 | 5.0 |
| Sodium lauroyl sulfosuccinate | 3 | 3 | 3 | 3 | 3 | — |
| Hydroxypropyl starch phosphate ester (structure XL) | 0.1 | 0.3 | 0.2 | 0.1 | 0.3 | 0.1 |
| Sodium carbomer | — | — | — | 0.2 | — | — |
| Polyquaternium-10 | 0.3 | 0.2 | 0.2 | 0.3 | 0.3 | 0.3 |
| Guar hydroxypropyl trimonium chloride | 0.1 | 0.1 | 0.2 | 0.1 | 0.1 | 0.1 |
| PEG-3 distearate | 1.5 | — | — | — | — | 1.5 |
| Glycol distearate + glycerol + laureth-4 + cocamidopropylbetaine | — | 4 | — | — | — | — |
| Glycol distearate + laureth-4 + cocamidopropylbetaine | — | — | 4 | — | — | — |
| Glycol distearate + cocoglucoside + glyceryl oleate + glyceryl stearate | — | — | — | 4 | — | — |
| PEG-40 hydrogenated castor oil | 0.2 | 0.2 | 0.2 | 0.2 | 0.2 | 0.2 |

|  | | | | | | |
|---|---|---|---|---|---|---|
| Sodium salicylate | 0.4 | 0.4 | 0.4 | 0.4 | 0.4 | 0.4 |
| Sodium benzoate | 0.4 | 0.4 | 0.4 | 0.4 | 0.4 | 0.4 |
| Perfume | q.s. | q.s. | q.s. | q.s. | q.s. | q.s. |
| Water | ad 100 | ad 100 | ad 100 | ad 100 | ad 100 | ad 100 |
|  | 7 | 8 | 9 | 10 | 11 | 12 |
| Sodium lauryl ether sulfate | 9 | 9 | 9 | 9 | — | 11 |
| Sodium myristyl ether sulfate | — | — | — | — | 8 | — |
| Cocamidopropylbetaine | 4 | 4 | 4 | 4 | 4 | 5.0 |
| Sodium lauroyl sulfosuccinate | 3 | 3 | 3 | 3 | 2 | — |
| Hydroxypropyl starch phosphate ester (structure XL) | 0.1 | 0.2 | 0.4 | 0.2 | 0.3 | 0.1 |
| Sodium carbomer | — | — | — | 0.2 | — | — |
| Guar hydroxypropyl trimonium chloride | 0.2 | 0.3 | 0.4 | 0.3 | 0.2 | 1.3 |
| PEG-3 distearate | 1.5 | — | — | — | — | 1.5 |
| Glycol distearate + glycerol + laureth-4 + cocamidopropylbetaine | — | 4 | — | — | — | — |
| Glycol distearate + laureth-4 + cocamidopropylbetaine | — | — | 4 | — | — | — |
| Glycol distearate + cocoglucoside + glyceryl oleate + glyceryl stearate | — | — | — | 4 | — | — |
| PEG-40 hydrogenated castor oil | 0.2 | 0.2 | 0.2 | 0.2 | 0.2 | 0.2 |
| Sodium salicylate | 0.4 | 0.4 | 0.4 | 0.4 | 0.4 | 0.4 |
| Sodium benzoate | 0.4 | 0.4 | 0.4 | 0.4 | 0.4 | 0.4 |
| Perfume | q.s. | q.s. | q.s. | q.s. | q.s. | q.s. |
| Water | ad 100 | ad 100 | ad 100 | ad 100 | ad 100 | ad 100 |

The invention claimed is:

1. A composition which is suitable for cleansing hair and comprises
   (a) one or more pregelatinized, cross-linked starch derivatives;
   (b) one or more cationic polymers which comprise at least one polymeric quatemized ammonium salt of hydroxyethylcellulose which has been modified with a trimethylammonium-substituted epoxide; and
   (c) one or more nonionic, amphoteric or anionic surfactants which comprise at least one surfactant selected from fatty acid salts of sodium, alkyl sulfates, alkyl ether sulfates, alkane- and alkylbenzenesulfonates, sulfoacetates, sulfobetaines, sarcosinates, amidosulfobetaines, sulfosuccinates, sulfo-succinic half-esters, alkylether carboxylates, protein fatty acid condensates, alkyl betaines, amidobetaines, and fatty acid alkanolamides.

2. The composition of claim 1, wherein (a) comprises a hydroxypropylated phosphate ester.

3. The composition of claim 1, wherein (a) comprises hydroxypropyl distarch phosphate.

4. The composition of claim 1, wherein (c) comprises at least one of an alkylamidopropyl betaine and an ethoxylated and sulfated fatty alcohol having from 12 to 14 carbon atoms.

5. The composition of claim 1, wherein (c) comprises an alkylamidopropyl betaine and an ethoxylated and sulfated fatty alcohol having from 12 to 14 carbon atoms.

6. The composition of claim 1, wherein the composition comprises from 0.3% to 15% by weight of (a).

7. The composition of claim 6, wherein the composition comprises from 0.2% to 8% by weight of (b).

8. The composition of claim 7, wherein the composition comprises from 5% to 20% by weight of one or more anionic surfactants.

9. The composition of claim 1, wherein the composition is present as a shampoo.

10. A hair shampoo which comprises
    (a) from 0.2% to 10% by weight of one or more pregelatinized, cross-linked starch derivatives;
    (b) from 0.5% to 5% by weight of one or more cationic polymers which comprise at least one of a polymeric quatemized ammonium salt of hydroxyethylcellulose which has been modified with a trimethylammonium-substituted epoxide; and
    (c) at least one of (i) from 5% to 20% by weight of one or more anionic surfactants which comprise at least one surfactant selected from fatty acid salts of sodium, alkyl sulfates, alkyl ether sulfates, alkane- and alkylbenzenesulfonates, sulfoacetates, sulfosuccinates, sulfo-succinic half-esters and alkylether carboxylates, and (ii) from 1% to 10% by weight of one or more amphoteric surfactants which comprise at least one surfactant selected from alkylbetaines and amidobetaines.

11. The shampoo of claim 10, wherein (a) comprises hydroxypropyl distarch phosphate.

12. The shampoo of claim 11, wherein (c) comprises an alkylamidopropyl betaine and an ethoxylated and sulfated fatty alcohol having from 12 to 14 carbon atoms.

13. A hair shampoo which comprises
    (a) from 0.5% to 10% by weight of hydroxypropyl distarch phosphate;
    (b) from 0.3% to 5% by weight of one or more of a polymeric quatemized ammonium salt of hydroxyethylcellulose which has been modified with a trimethylammonium-substituted epoxide; and
    (c) (i) from 5% to 20% by weight of one or more anionic surfactants which comprise at least one of sodium laureth sulfate and disodium laureth sulfosuccinate, and (ii) from 1% to 10% by weight of one or more amphoteric surfactants which comprise at least one surfactant selected from alkylbetaines and amidobetaines.

14. The shampoo of claim 13, wherein (b) further comprises guar hydroxypropyl trimonium chloride.

15. A method of improving at least one of the combability, the volume, the body, the shine and the feel of hair, wherein the method comprises applying to the hair the composition of claim 1.

16. The method of claim 15, wherein at least one of the volume, the body and the shine of the hair is improved.

17. A method of improving at least one of the volume, the body and the shine of hair, wherein the method comprises applying to the hair the shampoo of claim 13.

* * * * *